United States Patent [19]
Hall

[11] 3,963,020
[45] June 15, 1976

[54] URINAL FOR HUMAN FEMALES

[76] Inventor: Kenneth F. Hall, 9205 W. 73rd Place, Arvada, Colo. 80005

[22] Filed: Feb. 7, 1975

[21] Appl. No.: 547,787

Related U.S. Application Data

[63] Continuation of Ser. No. 418,357, Nov. 23, 1973, abandoned.

[52] U.S. Cl. .................................. 128/2 F; 4/110; 128/295
[51] Int. Cl.² .................. A61B 10/00; E03D 13/00; A61G 9/00
[58] Field of Search ................ 128/2 F, 295; 4/110

[56] References Cited
UNITED STATES PATENTS

| | | | |
|---|---|---|---|
| 137,214 | 3/1873 | Knight et al. | 4/110 |
| 698,419 | 4/1902 | Taylor | 4/110 |
| 2,084,788 | 6/1937 | Anderson | 4/110 UX |
| 2,542,276 | 2/1951 | Felts | 4/110 |
| 2,582,398 | 1/1952 | Siegenthal | 4/110 |
| 2,594,339 | 4/1952 | Nugent | 4/110 |
| 3,161,891 | 12/1964 | Bauman | 4/110 |
| 3,335,714 | 8/1967 | Giesy | 128/2 F |
| 3,432,866 | 3/1969 | Schwartz | 4/110 |
| 3,473,172 | 10/1969 | Friedman et al. | 4/110 |
| 3,815,581 | 6/1974 | Levin | 128/2 F |

FOREIGN PATENTS OR APPLICATIONS

| | | | |
|---|---|---|---|
| 100,854 | 1/1899 | Germany | 128/295 |
| 1,393 | 1899 | United Kingdom | 4/110 |

*Primary Examiner*—Kyle L. Howell
*Attorney, Agent, or Firm*—Ancel W. Lewis, Jr.

[57] ABSTRACT

A disposable urinal for collecting and containing human female urine that enables a female to void while lying supine for collecting a urine specimen or in a sitting position for laboratory analysis and the like. The urinal has a lower receptacle section for storing the urine, a narrowed neck portion and outwardly extending, diverging cuplike portions forming an inlet opening that fits against the body tissue around and spaced from the urethral opening between the labia without direct contact with the urethral opening and against the mucous membrane of the anterior vaginal wall of the female body. The receptacle section has a contour in relation to the neck and inlet opening and a flat bottom that affords maximum volume when disposed in the filling position and also has volume indicia to indicate the amount contained therein.

5 Claims, 11 Drawing Figures

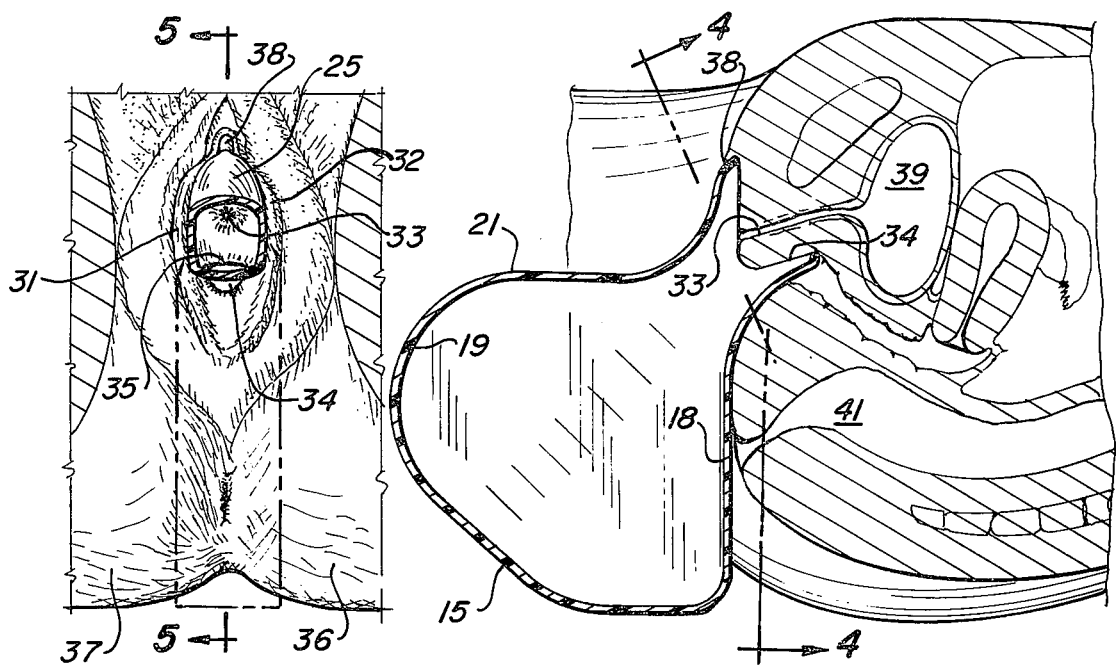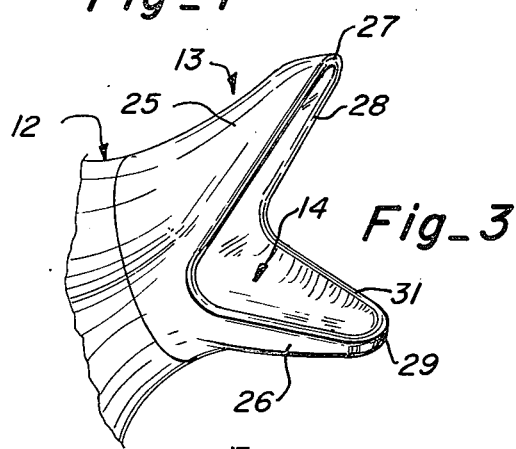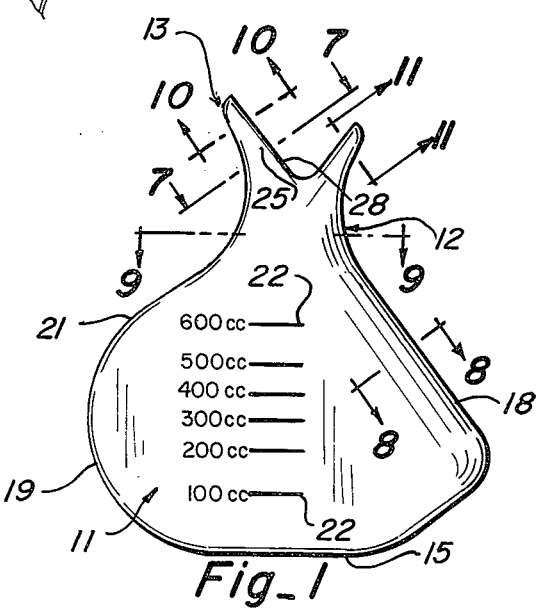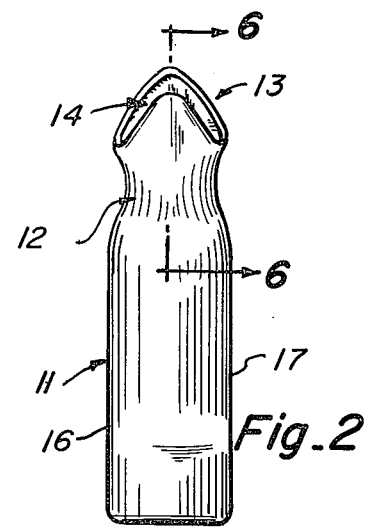

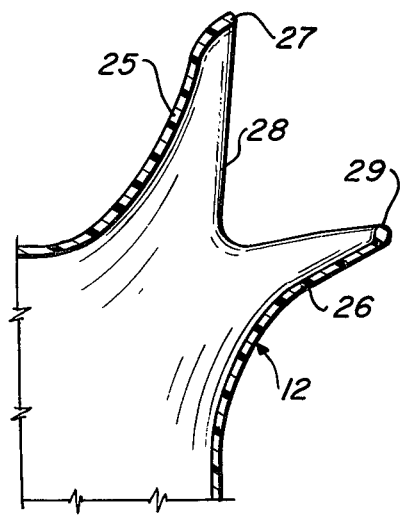
Fig_6
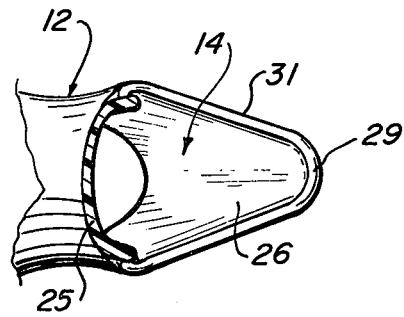
Fig_7
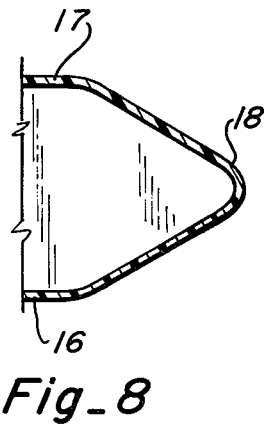
Fig_8
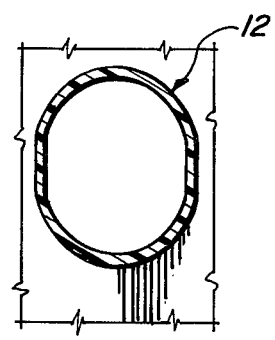
Fig_9
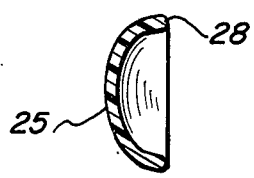
Fig_10
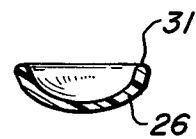
Fig_11

URINAL FOR HUMAN FEMALES

This is a continuation of application Ser. No. 418,357, filed Nov. 23, 1973, now abandoned.

BACKGROUND OF THE INVENTION

This invention relates generally to urinals and more particularly to a novel disposable urinal for human females.

The most common technique presently in use in hospitals and doctors' offices for taking urine specimens is a bed pan or specimen bottle which involves direct contact with the urethral opening of the female and is thereby subject to body contamination, spillage, and possible discomfort. For relieving oneself while lying supine in a hospital bed, a bed pan is most frequently used and this technique has drawbacks from the standpoint of possible spillage, odor and it is generally cumbersome.

Accordingly, it is a general object of this invention to provide a urinal for enabling female patients to void while lying supine or to collect a urine specimen in the sitting position for laboratory analysis or the like and is shaped for containing maximum volume in the filling position.

Another object of this invention is to provide a novel disposable urinal for females that does not come into direct contact with the urethral opening, is comfortable to use, and is beneficial in avoiding or controlling possible infections.

Yet a further object of this invention is to provide a novel urinal that affords a psychological benefit to a female patient by allowing her self-care without undue exposure or discomfort.

Yet another object of this invention is to provide a disposable urinal for females that can be made as a onepiece body from a plastic material characterized by having outwardly diverging cuplike portions with a soft pliable lip defining an inlet opening that cups directly against the users body in such a way as to prevent spillage or leakage as well as contain the urine in indicated volumes.

Other objects, advantages and capabilities of the present invention will become more apparent as the description proceeds taken in conjunction with the accompanying drawings, in which:

FIG. 1 is a side elevation view of a disposable urinal made in accordance with the present invention disposed in an upright position on a support surface;

FIG. 2 is an end elevation view thereof;

FIG. 3 is a perspective view of the upper head section thereof;

FIG. 4 is a front elevation view of the head section positioned for use on a human female with the urinal being broken along lines 4—4 of FIG. 5;

FIG. 5 is a vertical sectional view taken along lines 5—5 of FIG. 4;

FIG. 6 is a sectional view taken along lines 6—6 of FIG. 2 and inclined as shown in FIG. 5 and to approximate full scale size;

FIG. 7 is a sectional view taken along lines 7—7 of FIG. 1 and to approximate full scale size;

FIG. 8 is a sectional view taken along lines 8—8 of FIG. 1;

FIG. 9 is a sectional view taken along lines 9—9 of FIG. 1;

FIG. 10 is a sectional view taken along lines 10—10 of FIG. 1;

FIG. 11 is a sectional view taken along lines 11—11 of FIG. 1.

Referring now to the drawings in FIGS. 1 through 4, there is shown a disposable urinal made as a single-piece or unitary body from a molded plastic material and in general comprises a lower receptacle section 11, a narrowed neck section 12 extending up from the receptacle section 11 and terminating in a head section 13 having an inlet or receiving opening 14.

The receptacle section 11 comprises a flat bottom wall 15, a pair of opposed flat walls 16 and 17 arranged parallel to one another and another pair of opposed walls 18 and 19, with these walls upstanding from the bottom 15. The flat bottom wall 15 is adapted to support the wall portions of receptacle section 11 in an upright manner on a flat supporting surface. The wall portions 18 and 19 are shaped in such a way as to afford maximum fill volume for the receptacle section when positioned on the female body as illustrated in FIG. 5. To this end, a part of the wall portion 18 extends out at an angle from the bottom 15, curves and then inclines back toward the neck section 12. This shape allows the backturned part that is V-shaped to fit against the area of the rectum 41 in a substantially vertical orientation in the in-use position. The other wall portion 19 opposite wall portion 18 is outwardly concave from the bottom and has a portion 21 that merges with the neck section 12 that is essentially a top wall in the in-use filling position.

The receptacle section 11 is preferably made of a translucent material making it possible to see the depth of the urine contents and as shown it has a volume indicia 22 to measure about 600 cc of urine. While a 600 cc receptacle capacity as shown is preferred for hospital use it is understood that for some applications such as for laboratory specimens a 150 cc receptacle would be adequate. The shape of the receptacle section as shown would be the same but only a smaller volume and volume indicia in increments up to 150 cc.

The front wall 18 is outwardly tapered or generally V-shaped terminating at a relatively narrow, rounded front edge to facilitate the placement of the receptacle section 11 in a depending manner between the buttocks of the human female body as best seen in FIGS. 4 and 5.

The neck section 12 is tubular and generally oval in transverse cross section as shown in FIG. 9 and merges with the wall portions of the receptacle section 11.

The head section 13 comprises a hollow annular support portion that is an extension of the neck section and a cuplike projecting portion 25 and another cuplike projecting portion 26 diverging out from the neck at an acute angle to one another. The angle shown is on the order of 80 degrees with the projecting portions extending substantially beyond the neck section 12. The projecting portions 25 and 26 are laterally concavely curved along the inside thereof and are widest and deepest at their ends where they are almost semicircular in transverse cross section and merge with the neck section 12. The projecting portions 25 and 26 gradually taper inwardly along the side edges and the depth decreases toward the outer extremity. Projection portion 25 terminates in a curved outer tip 27 and projection portion 26 terminates in a curved outer tip 29. As best seen in FIG. 2, this provides an essentially inverted U-shaped or parabolic-like lip 28 on portion 25 and lip 31 on portion 26. This lip on each projecting portion is shown to have a pair of laterally spaced lip portions that are separated to a maximum extent where they merge with diametrically opposed lip portions on the support portion from which the projecting portions extend and they then converge inwardly toward one another to a leading tip at a point remote from the hollow annular portion. These lips have a transverse cross section that is rounded on or radiused throughout the lengthwise extent thereof. This inner surface and the tip 28 of portion 25 forms a pour spout. The lips 28 and 31 merge at an outer rounded edge of the neck section 12 to form an endless or continuous lip edge that defines the boundary of the inlet opening into the neck section.

As with the receptacle section 11, the neck and head sections are made of a relatively soft, pliable molded plastic material affording torsional flexure so as to adapt to different patients and not irritate the body tissue to which it is applied.

The above described urinal and its use will now be described with reference to the parts of the human female body with which it is operatively associated with particular reference to FIGS. 4 and 5. The two labia 31 and 32 of the human female body are spread with the index and middle fingers and cuplike projecting portion 25 is positioned against or over the opening of the urethra 33. The other cuplike projecting portion 26 is inserted into a portion of the vagina 34 and is positioned against the anterior wall of the vagina so that the U-shaped lips of the projecting portions fit firmly against the body tissue. The tapered front wall 18 of the receptacle section fits between the buttocks 36 and 37 as shown in FIG. 4. The upper tip 27 is shown to terminate just below the clitoris 38. Other parts of the body shown in FIG. 5 include the bladder 39, rectum 41 and vagina 42. In use, the urinal is pushed up and in while voiding and left in place long enough while voiding to prevent spilling. The head section is inserted into place at one angle of approach and then tilted or turned down through a relatively small angle to position it in place for voiding. The urinal may then be discarded after use.

By way of illustration, a urinal as above described constructed in accordance with the present invention had the following approximate dimensions:

| | | |
|---|---|---|
| Height of lip 28 from tip 27 to edge of neck | 1.5 | inches |
| Height of lip 31 from tip 29 to edge of neck | 1.125 | inches |
| Maximum width of lips 28 and 29 | 1.25 | inches |

Although the present invention has been described with a certain degree of particularity, it is understood that the present disclosure has been made by way of example and that changes in details of structure may be made without departing from the spirit thereof.

What is claimed is:

1. In a disposable urinal and urine specimen collector for adult human females, the combination comprising:
   A. a receptacle for containing urine; and
   B. a head section in flow communication with the receptacle, said head section having
      a. a tubular support portion having a laterally spaced first pair of lip portions, and
      b. a generally leaf-shaped upper cup portion supported at one end by the support portion and projecting away from the support portion,
         i. said upper cup portion being concavely curved along the inside surface forming a laterally spaced second pair of lip portions that are upper extensions of said first pair of lip portions and are separated from one another to a maximum extent where they merge with said first pair of lip portions, said second pair of lip portions converge inwardly toward one another from the support portion to a leading tip to cup against body tissue to which it is applied,
         ii. said upper cup portion having spacing between said second pair of lip portions no greater than about 1.25 inches and a length no greater than about 1.5 inches to lie entirely within the area between the labia and terminate below the clitoris of an adult human female body,
         iii. said upper cup portion being relatively shallow in relation to the length thereof and made of a generally soft pliable plastic material to afford a slight degree of flexure in relation to said support portion,
   c. a generally leaf-shaped lower cup portion supported at one end by the support portion and projecting away from the support portion,
      i. said lower cup portion being laterally concavely curved along the inside surface forming a laterally spaced third pair of lip portions that are lower extensions of said first pair of lip portions and are separated from one another to a maximum extent where they merge with said first pair of lip portions, said third pair of lip portions converge inwardly toward one another from the support portion to a leading tip to cup against body tissue to which it is applied,
      ii. said lower cup portion having a spacing between said third pair of lip portions no greater than about 1.25 inches and a length no greater than about 1.125 inches to extend under the pubic arch into a portion of the anterior vaginal wall and engage the mucous membrane of an adult human female body to block contamination of the urine from the vagina and rectum area thereof,
      iii. said lower cup portion being relatively shallow in relation to the length and made of a generally soft pliable plastic material to afford a slight degree of flexure in relation to said support portion,
   d. the second and third pairs of lip portions diverging away from the support portion at an angle to one another of about 80 degrees to closely conform to the angle of the pubic arch of the adult human female body,
   e. said first, second and third pairs of lip portions forming an endless body-engaging lip on the head section that seals against the body tissue to which it is applied throughout the entire perimeter thereof to avoid urine leakage during the use thereof.

2. In a disposable urinal and urine specimen collector as set forth in claim 1 wherein each of said upper and lower cup portions having the greatest depth at the supported end and gradually decrease in depth toward the associated tip.

3. In a disposable urinal specimen collector as set forth in claim 1 wherein said endless body-engaging lip is rounded in transverse cross section.

4. In a disposable urinal and urine specimen collector as set forth in claim 1 wherein said receptacle has a tapered converging wall portion that is a lower extension of said lower cup portion adapted to fit between the buttocks of the adult human female body.

5. In a disposable urinal and urine specimen collector as set forth in claim 1 wherein said receptacle and head section have substantially uniform thickness throughout, said receptacle being made of a translucent material to permit observation of the level of the fluid contents therein, said receptacle section having a flat bottom adapted to seat on a flat surface and a first pair of opposed wall portions and a second pair of opposed wall portions upstanding from the bottom, one of said wall portions tapering outwardly, said first pair of opposed wall portions being generally parallel to one another and the second pair of wall portions being shaped in relation to the position of the bottom and neck to afford maximum fill volume during the filling thereof said receptacle section having indicia arranged parallel to the bottom to indicate the volume contained therein.

* * * * *